(12) United States Patent
Chabrecek et al.

(10) Patent No.: US 6,521,352 B1
(45) Date of Patent: Feb. 18, 2003

(54) PROCESS FOR THE MODIFICATION OF A MATERIAL SURFACE

(75) Inventors: Peter Chabrecek, Riehen (CH); Dieter Lohmann, Münchenstein (CH)

(73) Assignee: Novartis AG, Basel (CH)

( * ) Notice: Subject to any disclaimer, the term of this patent is extended or adjusted under 35 U.S.C. 154(b) by 6 days.

(21) Appl. No.: 09/698,528

(22) Filed: Oct. 27, 2000

(30) Foreign Application Priority Data

Oct. 27, 1999 (EP) .............................. 99810976

(51) Int. Cl.$^7$ ............................... B32B 27/28
(52) U.S. Cl. .............. 428/522; 428/704; 428/423.1; 428/424.4; 351/160 H
(58) Field of Search ................ 428/522, 704, 428/423.1, 424.4; 351/160 H

(56) References Cited

FOREIGN PATENT DOCUMENTS

| WO | WO 94/06485 | 3/1994 |
|----|-------------|--------|
| WO | WO 95/04609 | 2/1995 |
| WO | WO 96/20795 | 7/1996 |
| WO | WO 96/20919 | 7/1996 |
| WO | WO 97/21497 | 6/1997 |
| WO | WO 97/49740 | 12/1997 |
| WO | WO 98/28026 | 7/1998 |
| WO | WO 99/57581 | 11/1999 |

OTHER PUBLICATIONS

Valint P.L. et.al.: "Surfac–Active Macromers for Coating of Contact Lens Polymers", Polymeric Materials Science and Engineering, Washinton, DC US, vol. 76, pp. 93–94, XP000931173, ISSN: 0743–0515.
European Search Report.

*Primary Examiner*—James J. Seidleck
*Assistant Examiner*—Melanie Bissett
(74) *Attorney, Agent, or Firm*—R. Scott Meece; Jian S. Zhou; Richard T. Gearhart

(57) ABSTRACT

The invention relates to a process for coating a material surface, comprising the steps of:

(a) providing a hydrophilic telomer of formula $$\text{(oligomer)-T} \quad (1),$$

wherein the variables are as defined in the claims, and (b) covalently binding the hydrophilic telomer to the material surface.

The coated articles that are obtainable by the process of the invention have desirable characteristics regarding adherence to the substrate, durability, hydrophilicity, wettability, biocompatibility and permeability and are thus useful for the manufacture of biomedical articles such as ophthalmic devices.

13 Claims, No Drawings

PROCESS FOR THE MODIFICATION OF A MATERIAL SURFACE

The present invention relates to a process for the manufacture of coated articles wherein the coating comprises a polymer having desirable characteristics regarding adherence to the substrate, durability, hydrophilicity, wettability, biocompatibility and permeability. More particular, the present invention relates to a process for the modification of the surface of an article, such as a biomedical material or article, especially a contact lens including an extended-wear contact lens wherein the articles are at least partly coated with a polymer having a "bottle-brush" type structure composed of tethered "hairy" chains.

A variety of different types of processes for preparing polymeric coatings on a substrate have been disclosed in the prior art. For example, U.S. Pat. No. 5,527,925 describes functionalized photoinitiators and also organic substrates such as contact lenses containing said photoinitiators covalently bound to their surface. In one embodiment of said disclosure, the so modified surface of the contact lens is further coated with a photopolymerizable ethylenically unsaturated monomer which is then polymerized by irradiation thus forming a novel substrate surface. With this method, however, it is not always possible to obtain the desired coating characteristics, for example wettability characteristics which are necessary for the surface of biomedical devices including contact lenses. In particular, the ability of the known materials to attract and stabilize a continuous layer of an aqueous solution, e.g. human body fluids such as tears or mucus layers, for a prolonged period of time which is an important feature for many biomedical applications is not yet satisfactory.

Surprisingly, it now has been found that articles, particularly biomedical devices such as contact lenses, with an improved wettability, water-retention ability and biocompatibility are obtained by first of all providing a monofunctional hydrophilic telomer having a bottle-brush type structure and then attaching the telomer to the material surface, for example, by reaction of its functional group with co-reactive groups being present on the material surface.

The present invention therefore in one aspect relates to a process for coating a material surface, comprising the steps of:

(a) providing a hydrophilic telomer of formula (oligomer)-T     (1), wherein

T is hydroxy, epoxy, amino, $C_1$–$C_6$-alkylamino, carboxy or a suitable carboxy derivative, for example a carboxylic acid ester or an acid halide, and (oligomer) is the radical of a telomer of formula

     (2), wherein (Alk) is $C_2$–$C_{12}$-alkylene which may be interrupted by —O— or —NH—, Q is a monovalent group that is suitable to act as a polymerization chain-reaction terminator, a and b are each independently of another an integer from 0 to 350, wherein the total of (a+b) is an integer from 2 to 350, and Z and Z' are each independently of the other a 1,2-ethylene radical derivable from a copolymerizable vinyl monomer by replacing the vinylic double bond by a single bond, which radical carries a hydrophilic side chain having a weight average molecular weight of ≧200; and (b) covalently binding the hydrophilic telomer to the material surface.

The following meanings and preferences apply to the variables contained in the definition of the hydrophilic telomer of formula (1):

T as carboxy derivative is for example a radical —C(O)OC$_1$–C$_4$-alkyl or —C(O)Cl. T is preferably hydroxy, amino or carboxy, more preferably amino or carboxy and in particular amino.

(Alk) is preferably $C_2$–$C_8$-alkylene, more preferably $C_2$–$C_6$-alkylene, even more preferably $C_2$–$C_4$-alkylene and particularly preferably 1,2-ethylene. The alkylene radical (alk) may be branched or preferably linear alkylene.

Q is for example hydrogen.

The total of (a+b) is preferably an integer from 2 to 150, more preferably from 5 to 100, even more preferably from 5 to 75 and particularly preferably from 5 to 50. In a preferred embodiment of the invention b is 0 and a is an integer from 2 to 350, preferably from 2 to 150, more preferably from 5 to 100, even more preferably from 5 to 75, and particularly preferably from 5 to 50.

A suitable 1,2-ethylene radical Z or Z' is, for example, a radical of formula

     (3)

wherein $R_1$ is hydrogen or $C_1$–$C_6$-alkyl or a radical —COOR';

R, R' and $R_2$ are each independently of the other hydrogen or $C_1$–$C_6$-alkyl; and $R_3$ is, for example, a non-ionic substituent selected from the group consisting of a radical —COO$Y_{10}$, wherein $Y_{10}$ is a radical —CH$_2$CH$_2$—O—(CH$_2$CH$_2$O)$_y$—E, E is hydrogen or $C_1$–$C_6$-alkyl and y is an integer from 3 to 24, or $Y_{10}$ is a radical —C$_2$–C$_6$-alkyl-NH—C(O)—O—G wherein —O—G is the radical of a saccharide or is a radical —O—(CH$_2$CH$_2$O)$_y$—E wherein E and y are each as defined above; and a radical —CON$Y_{11}Y_{12}$, wherein $Y_{11}$ is hydrogen or unsubstituted or, for example, hydroxy-substituted $C_1$–$C_{24}$-alkyl, and $Y_{12}$ is $C_1$–$C_{12}$-alkyl which is substituted by a radical —O—(CH$_2$CH$_2$O)$_y$—E and wherein E and y are as defined above; and a zwitter-ionic substituent of formula

—C(O)O—CH$_2$—CH(O$Y_{13}$)—CH$_2$—O—PO$_2^-$—(CH$_2$)$_2$—N(CH$_3$)$_3^+$, wherein $Y_{13}$ is the acyl radical of a higher fatty acid; or $R_3$ is a radical of formula —A-(oligomer$^1$)     (4), wherein A is a direct bond or is a radical of formula —C(O)—(A$_1$)$_n$—X—     (5a) or —(A$_2$)$_m$—NH—C(O)—X—     (5b); or —(A$_2$)$_m$—X—C(O)—     (5c); or —C(O)—NH—C(O)—X—     (5d); or —C(O)—X$_1$—(alk*)X—C(O)—     (5e); or A and $R_1$, together with the adjacent double bond, are a radical of formula

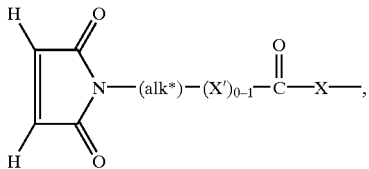
(5f)

$A_1$ is $-O-C_2-C_{12}$-alkylene which is unsubstituted or substituted by hydroxy, or is $-O-C_2-C_{12}$-alkylene-NH-C(O)- or $-O-C_2-C_{12}$-alkylene-O-C(O)-NH-$R_{33}$-NH-C(O)-, wherein $R_{33}$ is linear or branched $C_1-C_{18}$-alkylene or unsubstituted or $C_1-C_4$-alkyl- or $C_1-C_4$-alkoxy-substituted $C_6-C_{10}$-arylene, $C_7-C_{18}$-aralkylene, $C_6-C_{10}$-arylene-$C_1-C_2$-alkylene-$C_6-C_{10}$-arylene, $C_3-C_8$-cycloalkylene, $C_3-C_8$-cycloalkylene-$C_1-C_6$-alkylene, $C_3-C_8$-cycloalkylene-$C_1-C_2$-alkylene-$C_3-C_8$-cycloalkylene or $C_1-C_6$-alkylene-$C_3-C_8$-cycloalkylene-$C_1-C_6$-alkylene;

$A_2$ is $C_1-C_8$-alkylene; phenylene or benzylene;

m and n are each independently of the other the number 0 or 1;

X, $X_1$ and X' are each independently of the other a bivalent group $-O-$ or $-NR''$, wherein R'' is hydrogen or $C_1-C_6$-alkyl;

(alk*) is $C_2-C_{12}$-alkylene;

and (oligomer$^1$) is (i) the radical of a telomer of formula

(6a), wherein (alk) is $C_2-C_{12}$-alkylene, $Q_1$ is a monovalent group that is suitable to act as a polymerization chain-reaction terminator, p and q are each independently of another an integer from 0 to 350, wherein the total of (p+q) is an integer from 2 to 350, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

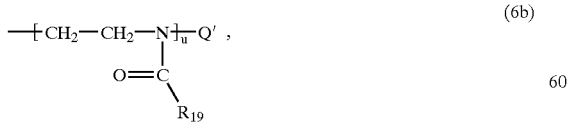
(6b)

wherein $R_{19}$ is hydrogen or unsubstituted or hydroxy-substituted $C_1-C_{12}$-alkyl, u is an integer from 2 to 250 and Q' is a radical of a polymerization initiator; or (iii) the radical of formula

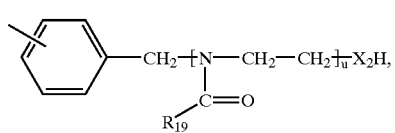
(6b')

wherein $X_2$ is $-O-$, $-NH-$ or $-NC_1-C_6$-alkyl- and $R_{19}$ and u are as defined above, or (iv) the radical of an oligomer of formula

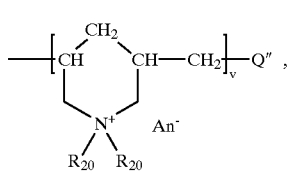
(6c)

wherein $R_{20}$ and $R_{20}'$ are each independently $C_1-C_4$-alkyl, An$^-$ is an anion, v is an integer from 2 to 250, and Q'' is a monovalent group that is suitable to act as a polymerization chain-reaction terminator; or (v) the radical of an oligopeptide of formula

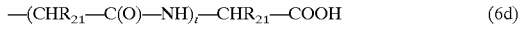
(6d)

or

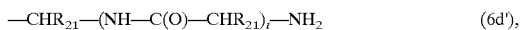
(6d'), wherein $R_{21}$ is hydrogen or $C_1-C_4$-alkyl which is unsubstituted or substituted by hydroxy, carboxy, carbamoyl, amino, phenyl, o-, m- or p-hydroxyphenyl, imidazolyl, indolyl or a radical $-NH-C(=NH)-NH_2$ and t is an integer from 2 to 250, or the radical of an oligopeptide based on proline or hydroxyproline; or (vi) the radical of a polyalkylene oxide of formula

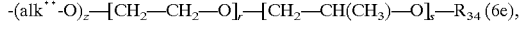
(6e), wherein $R_{34}$ is hydrogen or $C_1-C_{24}$-alkyl, (alk**) is $C_2-C_4$-alkylene, z is 0 or 1, r and s are each independently an integer from 0 to 250 and the total of (r+s) is from 2 to 250; or (vii) the radical of an oligosaccharide; subject to the provisos that A is not a direct bond if (oligomer) is a radical of formula (6a);

A is a radical of formula (5a), (5b) or (5d) or A and $R_1$, together with the adjacent double bond, are a radical of formula (5f) if (oligomer) is a radical of formula (6b), (6c), (6d) or (6e) or is the radical of an oligosaccharide;

A is a direct bond if (oligomer) is a radical of formula (6b'); and

A is a radical of formula (5c) or (5e) if (oligomer) is a radical of formula (6d').

The following preferences apply to the variables contained in the definition of the radicals of formula (3):

R is preferably hydrogen or methyl, in particular hydrogen.

R' is preferably hydrogen or $C_1-C_4$-alkyl, more preferably hydrogen or $C_1-C_2$-alkyl and particularly preferably hydrogen.

$R_1$ is preferably hydrogen, methyl or carboxyl, and particularly preferably hydrogen.

$R_2$ is preferably hydrogen or methyl.

One group of suitable radicals $R_3$ are those wherein $R_3$ is a radical $—COOY_{10}$, $—CONY_{11}Y_{12}$ or $—C(O)O—CH_2—CH(OY_{13})—CH_2—O—PO_2^-—(CH_2)_2—N(CH_3)_3^+$, wherein $Y_{10}$, $Y_{11}$, $Y_{12}$ and $Y_{13}$ are each as defined above. E is preferably hydrogen or $C_1$–$C_2$-alkyl, y is preferably an integer from 3 to 16, more preferably from 4 to 12, and in particular from 5 to 10. Examples of suitable saccharide substituents —O—G of the alkyl radical $Y_{10}$ that is substituted by —NH—C(O)—O—G are the radical of a mono- or disaccharide, for example glucose, acetyl glucose, methyl glucose, glucosamine, N-acetyl glucosamine, glucono lactone, mannose, galactose, galactosamine, N-acetyl galactosamine, fructose, maltose, lactose, fucose, saccharose or trehalose, the radical of an anhydrosaccharide such as levoglucosan, the radical of a glucosid such as octylglucosid, the radical of a sugar alcohol such as sorbitol, the radical of a sugar acid derivative such as lactobionic acid amide, or the radical of an oligosaccharide with a maximum of 8 sugar units, for example fragments of a cyclodextrin, starch, chitosan, maltotriose or maltohexaose. The saccharide radical —O—G is preferably the radical of a mono- or disaccharide or the radical of a cyclodextrin fragment with a maximum of 8 sugar units. Particular preferred saccharide radicals —O—G are the radical of trehalose or the radical of a cyclodextrin fragment. $Y_{11}$ is preferably hydrogen.

A preferred radical Z or Z' according to the invention is, for example, of the formula

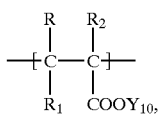

(3')

wherein for R, $R_1$, $R_2$ and $Y_{10}$ each the above given meanings and preferences apply. A particular preferred radical Z or Z' corresponds to the above formula (3'), wherein R and $R_1$ are each hydrogen, $R_2$ is hydrogen or methyl, and $Y_{10}$ is a radical $—CH_2CH_2—O—(CH_2CH_2O)_{4-12}—E$ or $—CH_2CH_2—NH—C(O)—O—G$, wherein —O—G is the radical of a mono- or disaccharide or the radical of an oligosaccharide and E is hydrogen or $C_1$–$C_2$-alkyl.

According to a further embodiment of the invention $R_3$ is a radical of the above formula (4) wherein the above-given meanings and the preferences given below apply.

X is preferably a bivalent group —O— or —NH—. X is particularly preferably the group —NH— if (oligomer¹) is a radical of formula (6a); (6c) or (6d), and is particularly preferably the group —O— if (oligomer¹) is a radical of formula (6b) or (6e) or is the radical of an oligosaccharide. X' is preferably —O— or —NH— and more preferably —NH—. $X_1$ is preferably —O— or —NH—.

$R_{33}$ as alkylene is preferably a linear or branched $C_3$–$C_{14}$alkylene radical, more preferably a linear or branched $C_4$–$C_{12}$alkylene radical and most preferably a linear or branched $C_6$–$C_{10}$-alkylene radical. Some preferred alkylene radicals are 1,4-butylene, 2,2-dimethyl-1,4-butylene, 1,5-pentylene, 2,2-dimethyl-1,5-pentylene, 1,6-hexylene, 2,2,3- or 2,2,4-trimethyl-1,5-pentylene, 2,2-dimethyl-1,6-hexylene, 2,2,3- or 2,2,4- or 2,2,5-trimethyl-1,6-hexylene, 2,2-dimethyl-1,7-heptylene, 2,2,3- or 2,2,4- or 2,2,5- or 2,2,6-trimethyl-1,7-heptylene, 1,8-octylene, 2,2-dimethyl-1,8-octylene and 2,2,3- or 2,2,4- or 2,2,5- or 2,2,6- or 2,2,7-trimethyl-1,8-octylene.

When $R_{33}$ is arylene, it is, for example, naphthylene or especially phenylene, each of which may be substituted, for example, by $C_1$–$C_4$-alkyl or by $C_1$–$C_4$-alkoxy. Preferably, $R_{33}$ as arylene is 1,3- or 1,4-phenylene that is unsubstituted or substituted by $C_1$–$C_4$-alkyl or by $C_1$–$C_4$-alkoxy in the ortho-position to at least one linkage site. Examples of substituted arylene are 1-methyl-2,4-phenylene, 1,5-dimethyl-2,4-phenylene, 1-methoxy-2,4-phenylene and 1-methyl-2,7-naphthylene.

$R_{33}$ as aralkylene is preferably naphthylalkylene and most preferably phenylalkylene. The alkylene group in aralkylene contains preferably from 1 to 12, more preferably from 1 to 6 and most preferably from 1 to 4 carbon atoms. Most preferably, the alkylene group in aralkylene is methylene or ethylene. Some examples are 1,3- or 1,4-benzylene, naphth-2-yl-7-methylene, 6-methyl-1,3- or -1,4-benzylene and 6-methoxy-1,3- or -1,4-benzylene.

When $R_{33}$ is cycloalkylene, it is preferably $C_5$–$C_6$-cycloalkylene and most preferably cyclohexylene that is unsubstituted or substituted by methyl. Some examples are 1,3-cyclobutylene, 1,3-cyclopentylene, 1,3- or 1,4-cyclohexylene, 1,3- or 1,4-cycloheptylene, 1,3- or 1,4- or 1,5-cyclooctylene, 4-methyl-1,3-cyclopentylene, 4-methyl-1,3-cyclohexylene, 4,4-dimethyl-1,3-cyclohexylene, 3-methyl- or 3,3-dimethyl-1,4-cyclohexylene, 3,5-dimethyl-1,3-cyclohexylene and 2,4-dimethyl-1,4-cyclohexylene.

When $R_{33}$ is cycloalkylene-alkylene, it is preferably cyclopentylene-$C_1$–$C_4$-alkylene and especially cyclohexylene-$C_1$–$C_4$-alkylene, each unsubstituted or mono- or poly-substituted by $C_1$–$C_4$-alkyl, especially methyl. More preferably, the group cycloalkylene-alkylene is cyclohexylene-ethylene and, most preferably, cyclohexylene-methylene, each unsubstituted or substituted in the cyclohexylene radical by from 1 to 3 methyl groups. Some examples are cyclopent-1-yl-3-methylene, 3-methyl-cyclopent-1-yl-3-methylene, 3,4-dimethyl-cyclopent-1-yl-3-methylene, 3,4,4-trimethyl-cyclopent-1-yl-3-methylene, cyclohex-1-yl-3- or -4-methylene, 3- or 4- or 5-methyl-cyclohex-1-yl-3- or -4-methylene, 3,4- or 3,5-dimethyl-cyclohex-1-yl-3- or -4-methylene and 3,4,5- or 3,4,4- or 3,5,5-trimethyl-cyclohex-1-yl-3- or -4-methylene.

When $R_{33}$ is alkylene-cycloalkylene-alkylene, it is preferably $C_1$–$C_4$-alkylene-cyclopentylene-$C_1$–$C_4$-alkylene and especially $C_1$–$C_4$-alkylene-cyclohexylene-$C_1$–$C_4$-alkylene, each unsubstituted or mono- or poly-substituted by $C_1$–$C_4$-alkyl, especially methyl. More preferably, the group alkylene-cycloalkylene-alkylene is ethylene-cyclohexylene-ethylene and, most preferably, is methylene-cyclohexylene-methylene, each unsubstituted or substituted in the cyclohexylene radical by from 1 to 3 methyl groups. Some examples are cyclopentane-1,3-dimethylene, 3-methyl-cyclopentane-1,3-dimethylene, 3,4-dimethyl-cyclopentane-1,3-dimethylene, 3,4,4-trimethyl-cyclopentane-1,3-dimethylene, cyclohexane-1,3- or -1,4-dimethylene, 3- or 4- or 5-methyl-cyclohexane-1,3- or -1,4-dimethylene, 3,4- or 3,5-dimethyl-cyclohexane-1,3- or -1,4-dimethylene, 3,4,5- or 3,4,4- or 3,5,5-trimethyl-cyclohexane-1,3- or -1,4-dimethylene.

$R_{33}$ as $C_3$–$C_8$-cycloalkylene-$C_1$–$C_2$-alkylene-$C_3$–$C_8$-cycloalkylene or $C_6$–$C_{10}$-arylene-$C_1$–$C_2$-alkylene-$C_6$–$C_{10}$-arylene is preferably $C_5$–$C_6$-cycloalkylene-methylene-$C_5$–$C_6$-cycloalkylene or phenylene-methylene-phenylene, each of which may be unsubstituted or substituted in the cycloalkyl or phenyl ring by one or more methyl groups.

The radical $R_{33}$ has a symmetrical or, preferably, an asymmetrical structure. A preferred group of radicals $R_{11}$, comprises those, wherein $R_{33}$ is linear or branched $C_6$–$C_{10}$alkylene; cyclohexylene-methylene or cyclohexylene-methylene-cyclohexylene each unsubstituted or substituted in the cyclohexyl moiety by from 1 to 3 methyl groups; or phenylene or phenylene-methylene-phenylene each unsubstituted or substituted in the phenyl moiety by methyl. The bivalent radical $R_{33}$ is derived preferably from a diisocyanate and most preferably from a diisocyanate selected from the group isophorone diisocyanate (IPDI), toluylene-2,4-diisocyanate (TDI), 4,4'-methylenebis(cyclohexyl isocyanate), 1,6diisocyanato-2,2,4-trimethyl-n-hexane (TMDI), methylenebis(phenyl isocyanate), methylenebis(cyclohexyl-4-isocyanate) and hexamethylene diisocyanate (HMDI).

Preferred meanings of $A_1$ are unsubstituted or hydroxy-substituted —O—$C_2$–$C_8$-alkylene or a radical —O—$C_2$–$C_6$-alkylene-NH—C(O)— and particularly —O—$(CH_2)_{2-4}$—, —O—$CH_2$—CH(OH)—$CH_2$— or a radical —O—$(CH_2)_{2-4}$—NH—C(O)—. A particularly preferred meaning of Al is the radical —O—$(CH_2)_2$—NH—C(O)—.

$A_2$ is preferably $C_1$–$C_6$-alkylene, phenylene or benzylene, more preferably $C_1$–$C_4$-alkylene and even more preferably $C_1$–$C_2$-alkylene. n is an integer of 0 or preferably 1. m is preferably an integer of 1. In case that (oligomer$^1$) is a radical of formula (6a), (6b), (6c), (6d) or (6e) or is the radical of an oligosaccharide, A preferably denotes a radical of formula (5a) or (5b) and particularly preferably a radical of formula (5a), wherein the above given meanings and preferences apply for the variables contained therein.

A preferred group of radicals Z or Z' according to the invention comprises radicals of the above formula (3), wherein $R_2$ is hydrogen or methyl, $R_1$ is hydrogen, methyl or carboxyl, R is hydrogen, and $R_3$ is a radical of the above formula (4) wherein A is a radical of the formula (5a) or (5b) and (oligomer$^1$) is a radical of formula (6a), (6b), (6c), (6d) or (6e) or is the radical of an oligosaccharide. An even more preferred group of radicals Z or Z' comprises radicals of the above formula (3), wherein $R_2$ is hydrogen or methyl, R and $R_1$ are each hydrogen, and $R_3$ is a radical of the formula (4), wherein A is a radical of the formula (5a) and (oligomer$^1$) is a radical of formula (6a). A further group of preferred radicals Z or Z' comprises radicals of formula (3), wherein $R_2$ is hydrogen or methyl, R and $R_1$ are each hydrogen, and $R_3$ is a radical of the formula (4), wherein A is a radical of formula (5e) above and (oligomer$^1$) is a radical of formula (6a).

(alk) and (alk*) are each independently preferably $C_2$–$C_8$-alkylene, more preferably $C_2$–$C_6$alkylene, even more preferably $C_2$–$C_4$-alkylene and particularly preferably 1,2-ethylene. The alkylene radicals (alk) and (alk*) may be branched or preferably linear alkylene radicals.

Q is for example hydrogen.

The total of (p+q) is preferably an integer from 2 to 150, more preferably from 5 to 100, even more preferably from 5 to 75 and particularly preferably from 10 to 50. In a preferred embodiment of the invention q is 0 and p is an integer from 2 to 250, preferably from 2 to 150, more preferably from 5 to 100, even more preferably from 5 to 75 and particularly preferably from 10 to 50.

Suitable hydrophilic substituents of the radicals B or B' may be non-ionic, anionic, cationic or zwitterionic substituents. Accordingly, the telomer chain of formula (5a) that contains monomer units B and/or B' may be a charged chain containing anionic, cationic and/or zwitterionic groups or may be an uncharged chain. In addition, the telomer chain may comprise a copolymeric mixture of uncharged and charged units. The distribution of the charges within the telomer, if present, may be random or blockwise.

In one preferred embodiment of the invention, the telomer radical of formula (6a) is composed solely of non-ionic monomer units B and/or B'. In another preferred embodiment of the invention, the telomer radical of formula (6a) is composed solely of ionic monomer units B and/or B', for example solely of cationic monomer units or solely of anionic monomer units. Still another preferred embodiment of the invention is directed to telomer radicals of formula (6a) comprising nonionic units B and ionic units B'.

Suitable non-ionic substituents of B or B' include for example a radical $C_1$–$C_6$-alkyl which is substituted by one or more same or different substituents selected from the group consisting of —OH, $C_1$–$C_4$-alkoxy and —$NR_{23}R_{23}'$, wherein $R_{23}$ and $R_{23}'$ are each independently of another hydrogen or unsubstituted or hydroxy-substituted $C_1$–$C_6$-alkyl or phenyl; phenyl which is substituted by hydroxy, $C_1$–$C_4$-alkoxy or —$NR_{23}R_{23}'$, wherein $R_{23}$ and $R_{23}'$ are as defined above; a radical —COOY, wherein Y is $C_1$–$C_{24}$-alkyl which is unsubstituted or substituted, for example, by hydroxy, $C_1$–$C_4$-alkoxy, —O—$Si(CH_3)_3$, —$NR_{23}R_{23}'$ wherein $R_{23}$ and $R_{23}'$ are as defined above, a radical —O—$(CH_2CH_2O)_{1-24}$—E wherein E is hydrogen or $C_1$–$C_6$-alkyl, or a radical —NH—C(O)—O—G, wherein —O—G is the radical of a saccharide with 1 to 8 sugar units or is a radical —O—$(CH_2CH_2O)_{1-24}$—E, wherein E is as defined above, or Y is $C_5$–$C_8$-cycloalkyl which is unsubstituted or substituted by $C_1$–$C_4$-alkyl or $C_1$–$C_4$-alkoxy, or is unsubstituted or $C_1$–$C_4$-alkyl- or $C_1$–$C_4$-alkoxy-substituted phenyl or $C_7$–$C_{12}$-aralkyl; —$CONY_1Y_2$ wherein $Y_1$ and $Y_2$ are each independently hydrogen, $C_1$–$C_{12}$-alkyl, which is unsubstituted or substituted for example by hydroxy, $C_1$–$C_4$-alkoxy or a radical —O—$(CH_2CH_2O)_{1-24}$—E wherein E is as defined above, or $Y_1$ and $Y_2$ together with the adjacent N-atom form a five- or six-membered heterocyclic ring having no additional heteroatom or one additional oxygen or nitrogen atom; a radical —$OY_3$, wherein $Y_3$ is hydrogen; or $C_1$–$C_{12}$-alkyl which is unsubstituted or substituted by —$NR_{23}R_{23}'$; or is a radical —C(O)—$C_1$–$C_4$-alkyl; and wherein $R_{23}$ and $R_{23}'$ are as defined above; or a five- to seven-membered heterocyclic radical having at least one N-atom and being bound in each case via said nitrogen atom.

Suitable anionic substituents of B or B' include for example $C_1$–$C_6$-alkyl which is substituted by —$SO_3H$, —$OSO_3H$, —$OPO_3H_2$ and —COOH; phenyl which is substituted by one or more same or different substituents selected from the group consisting of —$SO_3H$, —COOH, —OH and —$CH_2$—$SO_3H$; —COOH; a radical —$COOY_4$, wherein $Y_4$ is $C_1$–$C_{24}$-alkyl which is substituted for example by —COOH, —$SO_3H$, —$OSO_3H$, —$OPO_3H_2$ or by a radical —NH—C(O)—O—G' wherein G' is the radical of an anionic carbohydrate; a radical —$CONY_5Y_6$ wherein $Y_5$ is $C_1$–$C_{24}$-alkyl which is substituted by —COOH, —$SO_3H$, —$OSO_3H$, or —$OPO_3H_2$ and $Y_6$ independently has the meaning of $Y_5$ or is hydrogen or $C_1$–$C_{12}$-alkyl; or —$SO_3H$; or a salt thereof, for example a sodium, potassium, ammonium or the like salt thereof.

Suitable cationic substituents of B or B' include $C_1$–$C_{12}$-alkyl which is substituted by a radical —$NR_{23}R_{23}'R_{23}''^+An^-$, wherein $R_{23}$, $R_{23}''$ and $R_{23}''$ are each independently of another hydrogen or unsubstituted or hydroxy-substituted $C_1$–$C_6$-alkyl or phenyl, and $An^-$ is an anion; or a radical —$C(O)OY_7$, wherein $Y_7$ is $C_1$–$C_{24}$-alkyl which is substituted by —$NR_{23}R_{23}'R_{23}''^+An^-$ and is further unsubstituted or substituted for example by hydroxy, wherein $R_{23}$ $R_{23}'$, $R_{23}''$ and $An^-$ are as defined above.

Suitable zwitterionic substituents of B or B' include a radical —$R_{24}$—Zw, wherein $R_{24}$ is a direct bond or a functional group, for example a carbonyl, carbonate, amide, ester, dicarboanhydride, dicarboimide, urea or urethane group; and Zw is an aliphatic moiety comprising one anionic and one cationic group each.

The following preferences apply to the hydrophilic substituents of B and B':

(i) Non-ionic Substituents

Preferred alkyl substituents of B or B' are $C_1$–$C_4$-alkyl, in particular $C_1$–$C_2$-alkyl, which is substituted by one or more substituents selected from the group consisting of —OH and —$NR_{23}R_{23}'$, wherein $R_{23}$ and $R_{23}'$ are each independently of another hydrogen or $C_1$–$C_4$-alkyl, preferably hydrogen, methyl or ethyl and particularly preferably hydrogen or methyl, for example —$CH_2$—$NH_2$, —$CH_2$—$N(CH_3)_2$. Preferred phenyl substituents of B or B' are phenyl which is substituted by —$NH_2$ or $N(C_1$–$C_2$-alkyl$)_2$, for example o-, m- or p-aminophenyl. In case that the hydrophilic substituent of B or B' is a radical —COOY, Y as optionally substituted alkyl is preferably $C_1$–$C_{12}$-alkyl, more preferably $C_1$–$C_6$-alkyl, even more preferably $C_1$–$C_4$-alkyl and particularly preferably $C_1$–$C_2$-alkyl, each of which being unsubstituted or substituted as mentioned above. In case that the alkyl radical Y is substituted by —$NR_{23}R_{23}'$, the above-given meanings and preferences apply for $R_{23}$ and $R_{23}'$. Examples of suitable saccharide substituents —O—G of the alkyl radical Y that is substituted by —NH—C(O)—O—G are the radical of a mono- or disaccharide, for example glucose, acetyl glucose, methyl glucose, glucosamine, N-acetyl glucosamine, glucono lactone, mannose, galactose, galactosamine, N-acetyl galactosamine, fructose, maltose, lactose, fucose, saccharose or trehalose, the radical of an anhydrosaccharide such as levoglucosan, the radical of a glucosid such as octylglucosid, the radical of a sugar alcohol such as sorbitol, the radical of a sugar acid derivative such as lactobionic acid amide, or the radical of an oligosaccharide with a maximum of 8 sugar units, for example fragments of a cyclodextrin, starch, chitosan, maltotriose or maltohexaose. The radical —O—G preferably denotes the radical of a mono- or disaccharide or the radical of a cyclodextrin fragment with a maximum of 8 sugar units. Particular preferred saccharide radicals —O—G are the radical of trehalose or the radical of a cyclodextrin fragment. In case that the alkyl radical Y is substituted by a radical —O—($CH_2CH_2O)_{1-24}$—E or —NH—C(O)—O—G wherein —O—G is —O—($CH_2CH_2O)_{1-24}$—E, the number of ($CH_2CH_2O$) units is preferably from 1 to 12 in each case and more preferably from 2 to 8. E is preferably hydrogen or $C_1$–$C_2$-alkyl. Y as $C_5$–$C_8$-cycloalkyl is for example cyclopentyl or preferably cyclohexyl, each of which being unsubstituted or substituted for example by 1 to 3 $C_1$–$C_2$-alkyl groups. Y as $C_7$–$C_{12}$-aralkyl is for example benzyl.

Preferred nonionic radicals —COOY are those wherein Y is $C_1$–$C_6$-alkyl; or $C_2$–$C_6$-alkyl which is substituted by one or two substituents selected from the group consisting of hydroxy;; $C_1$–$C_2$-alkoxy; —O—Si($CH_3)_3$; and —$NR_{23}R_{23}'$ wherein $R_{23}$ and $R_{23}'$ are each independently of another hydrogen or $C_1$–$C_4$-alkyl; or Y is a radical —$CH_2CH_2$—O—($CH_2CH_2O)_{1-12}$—E wherein E is hydrogen or $C_1$–$C_2$-alkyl; or is a radical —$C_2$–$C_4$-alkylene-NH—C(O)—O—G, wherein —O—G is the radical of a saccharide.

More preferred non-ionic radicals —COOY are those wherein Y is $C_1$–$C_4$-alkyl; or $C_2$–$C_4$-alkyl which is substituted by one or two substituents selected from the group consisting of —OH and —$NR_{23}R_{23}'$ wherein $R_{23}$ and $R_{23}'$ are each independently of another hydrogen or $C_1$–$C_2$-alkyl; or a radical —$CH_2CH_2$—O—($CH_2CH_2O)_{1-12}$—E wherein E is hydrogen or $C_1$–$C_2$-alkyl; or is a radical —$C_2$–$C_4$-alkylene-NH—C(O)—O—G wherein —O—G is the radical of a saccharide.

Particularly preferred radicals —COOY comprise those wherein Y is $C_1$–$C_2$-alkyl, particularly methyl; or $C_2$–$C_3$-alkyl, which is unsubstituted or substituted by hydroxy or N,N-di-$C_1$–$C_2$-alkylamino, or is a radical —$C_2$–$C_3$-alkylene-NH—C(O)—O—G wherein —O—G is the radical of trehalose or the radical of a cyclodextrin fragment with a maximum of 8 sugar units.

Preferred non-ionic substituents —C(O)—$NY_1Y_2$ of B or B' are those wherein $Y_1$ and $Y_2$ are each independently of the other hydrogen or $C_1$–$C_6$-alkyl which is unsubstituted or substituted by hydroxy; or $Y_1$ and $Y_2$ together with the adjacent N-atom form a heterocyclic 6-membered ring having no further heteroatom or having one further N- or O-atom. Even more preferred meanings of $Y_1$ and $Y_2$, independently of each other, are hydrogen or $C_1$–$C_4$-alkyl which is unsubstituted or substituted by hydroxy; or $Y_1$ and $Y_2$ together with the adjacent N-atom form a N—$C_1$–$C_2$-alkylpiperazino or morpholino ring. Particularly preferred non-ionic radicals —C(O)—$NY_1Y_2$ are those wherein $Y_1$ and $Y_2$ are each independently of the other hydrogen or $C_1$–$C_2$-alkyl; or $Y_1$ and $Y_2$ together with the adjacent N-atom form a morpholino ring.

Preferred non-ionic substituents —$OY_3$ of B or B' are those wherein $Y_3$ is hydrogen, $C_1$–$C_4$-alkyl which is unsubstituted or substituted by —$NH_2$ or —$N(C_1$–$C_2$-alkyl$)_2$, or is a group —C(O)$C_1$–$C_2$-alkyl. $Y_3$ is particularly preferred hydrogen or acetyl.

Preferred non-ionic heterocyclic substituents of B or B' are a 5- or 6-membered heteroaromatic or heteroaliphatic radical having one N-atom and in addition no further heteroatom or an additional N- or O- heteroatom, or is a 5 to 7-membered lactame. Examples of such heterocyclic radicals are N-pyrrolidonyl, 2- or 4-pyridinyl, 2-methyl pyridin-5-yl, 2-, 3- oder 4-hydroxypyridinyl, N-ϵ-caprolactamyl, N-imidazolyl, 2-methylimidazol-1-yl, N-morpholinyl or 4-N-methylpiperazin-1-yl, particularly N-morpholinyl or N-pyrrolidonyl.

A group of preferred non-ionic substituents of B or B' comprises $C_1$–$C_2$-alkyl, which is unsubstituted or substituted by —OH or —$NR_{23}R_{23}'$, wherein $R_{23}$ and $R_{23}'$ are each independently of the other hydrogen or $C_1$–$C_2$-alkyl; a radical —COOY wherein Y is $C_1$–$C_4$-alkyl; $C_2$–$C_4$-alkyl which is substituted by —OH, —$NR_{23}R_{23}'$ wherein $R_{23}$ and $R_{23}'$ are each independently of another hydrogen or $C_1$–$C_2$-alkyl, or Y is a radical —$C_2$–$C_4$-alkylene-NH—C(O)O—G wherein —O—G is the radical of a saccharide; a radical —C(O)—$NY_1Y_2$, wherein $Y_1$ and $Y_2$ are each independently of the other hydrogen or $C_1$–$C_6$-alkyl which is unsubstituted or substituted by hydroxy, or $Y_1$ and $Y_2$ together with the adjacent N-atom form a heterocyclic 6-membered ring having no further heteroatom or having one further N— or O-atom; a radical —$OY_3$, wherein $Y_3$ is hydrogen, $C_1$–$C_4$-alkyl which is unsubstituted or substituted by —$NH_2$ or —$N(C_1$–$C_2$-alkyl$)_2$, or is a group —C(O)$C_1$–$C_2$-alkyl; or a 5- or 6-membered heteroaromatic or heteroaliphatic radical having one N-atom and in addition no further heteroatom or an additional N-, O- or S-heteroatom, or a 5 to 7-membered lactame.

A group of more preferred non-ionic substituents of B or B' comprises a radical —COOY, wherein Y is $C_1$–$C_2$-alkyl, $C_2$–$C_3$-alkyl, which is substituted by hydroxy, amino or N,N-di-$C_1$–$C_2$-alkylamino, or is a radical —$C_2$–$C_4$-alkylene-NH—C(O)—O—G wherein —O—G is the radical of trehalose or a cyclodextrin fragment with a maximum of 8 sugar units; a radical —CO—$NY_1Y_2$, wherein $Y_1$ and $Y_2$ are each independently of the other hydrogen or $C_1$–$C_4$-alkyl which is unsubstituted or substituted by hydroxy, or $Y_1$ and $Y_2$ together with the adjacent N-atom form a N—$C_1$–$C_2$-alkylpiperazino or morpholino ring; or a heterocyclic radical selected from the group consisting of N-pyrrolidonyl, 2- or 4-pyridinyl, 2-methylpyridin-5-yl, 2-, 3- oder 4-hydroxypyridinyl, N-ε-caprolactamyl, N-imidazolyl, 2-methylimidazol-1-yl, N-morpholinyl and 4-N-methylpiperazin-1-yl.

A particularly preferred group of non-ionic substituents of B or B' comprises the radicals —$CONH_2$, —$CON(CH_3)_2$,

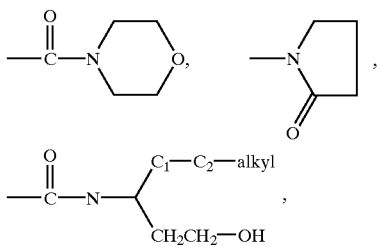

—CONH—$(CH_2)_2$—OH, —COO—$(CH_2)_2$—$N(CH_3)_2$, and —COO$(CH_2)_{2-4}$—NHC(O)—O—G wherein —O—G is the radical of trehalose.

(ii) Anionic Substituents

Preferred anionic substituents of B or B' are $C_1$–$C_4$-alkyl, in particular $C_1$–$C_2$-alkyl, which is substituted by one or more substituents selected from the group consisting of —$SO_3H$ and —$OPO_3H_2$, for example —$CH_2$—$SO_3H$; phenyl which is substituted by —$SO_3H$ or sulfomethyl, for example o-, m- or p-sulfophenyl or o-, m- or p-sulfomethylphenyl; —COOH; a radical —$COOY_4$, wherein $Y_4$ is $C_2$–$C_6$-alkyl which is substituted by —COOH, —$SO_3H$, —$OSO_3H$, —$OPO_3H_2$, or by a radical —NH—C(O)—O—G' wherein G' is the radical of lactobionic acid, hyaluronic acid or sialic acid, in particular $C_2$–$C_4$-alkyl which is substituted by —$SO_3H$ or —$OSO_3H$; a radical —$CONY_5Y_6$ wherein $Y_5$ is $C_1$–$C_6$-alkyl substituted by sulfo, in particular $C_2$–$C_4$-alkyl substituted by sulfo, and $Y_6$ is hydrogen, for example the radical —C(O)—NH—$C(CH_3)_2$—$CH_2$—$SO_3H$; or —$SO_3H$; or a suitable salt thereof. Particular preferred anionic substituents of B or B' are —COOH, —$SO_3H$, o-, m- or p-sulfophenyl, o-, m- or p-sulfomethylphenyl or a radical —$CONY_5Y_6$ wherein $Y_5$ is $C_2$–$C_4$-alkyl substituted by sulfo, and $Y_6$ is hydrogen.

(iii) Cationic Substituents

Preferred cationic substituents of B or B' are $C_1$–$C_4$-alkyl, in particular $C_1$–$C_2$-alkyl, which is in each case substituted by —$NR_{23}R_{23}'R_{23}''^+An^-$; or a radical —C(O)$OY_7$ wherein $Y_7$ is $C_2$–$C_6$-alkyl in particular $C_2$–$C_4$-alkyl, which is in each case substituted by —$NR_{23}R_{23}'R_{23}''^+An^-$ and is further unsubstituted or substituted by hydroxy. $R_{23}$, $R_{23}'$ and $R_{23}''$ are each independently of another preferably hydrogen or $C_1$–$C_4$-alkyl, more preferably methyl or ethyl and particularly preferably methyl. Examples of suitable anions $An^-$ are $Hal^-$, wherein Hal is halogen, for example $Br^-$, $F^-$, $J^-$ or particularly $Cl^-$, furthermore $HCO_3^-$, $CO_3^{2-}$, $H_2PO_3^-$, $HPO_3^{2-}$, $PO_3^{3-}$, $HSO_4^-$, $SO_4^{2-}$ or the radical of an organic acid such as $OCOCH_3^-$ and the like. A particularly preferred cationic substituent of B or B' is a radical —C(O)$OY_7$ wherein $Y_7$ is $C_2$–$C_4$-alkyl, which is substituted by —$N(C_1$–$C_2$-alkyl$)_3^+An^-$ and is further substituted by hydroxy, and $An^-$ is an anion, for example the radical —C(O)O—$CH_2$—CH(OH)—$CH_2$—$N(CH_3)_3^+An^-$.

(iv) Zwitterionic Substituents —$R_{24}$—Zw $R_{24}$ is a preferably a carbonyl, ester or amide functional group and more preferably an ester group —C(O)—O—.

Suitable anionic groups of the moiety Zw are for example —$COO^-$, —$SO_3^-$, —$OSO_3^-$, —$OPO_3H^-$ or bivalent —O—$PO_2^-$— or —O—$PO_2^-$—O—, preferably a group —$COO^-$ or —$SO_3^-$ or a bivalent group —O—$PO_2^-$—, and in particular a group —$SO_3^-$. Suitable cationic groups of the moiety Zw are for example a group —$NR_{23}R_{23}'R_{23}''^+$ or a bivalent group —$NR_{23}R_{23}'^+$—, wherein $R_{23}$, $R_{23}'$ and $R_{23}''$ are as defined above, and are each independently of the other, preferably hydrogen or $C_1$–$C_6$-alkyl, preferably hydrogen or $C_1$–$C_4$-alkyl and most preferably each methyl or ethyl.

The moiety Zw is for example $C_2$–$C_{30}$-alkyl, preferably $C_2$–$C_{12}$-alkyl, and more preferably $C_3$–$C_8$-alkyl, which is in each case uninterrupted or interrupted by —O— and substituted or interrupted by one of the above-mentioned anionic and cationic groups each, and, in addition, is further unsubstituted or substituted by a radical —$OY_8$, wherein $Y_8$ is hydrogen or the acyl radical of a carboxylic acid.

$Y_8$ is preferably hydrogen or the acyl radical of a higher fatty acid.

Zw is preferably $C_2$–$C_{12}$-alkyl and even more preferably $C_3$–$C_8$-alkyl which is substituted or interrupted by one of the above-mentioned anionic and cationic groups each, and in addition may be further substituted by a radical —$OY_8$.

A preferred group of zwitter-ionic substituents —$R_{24}$—Zw corresponds to the formula

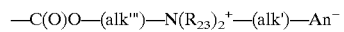

or

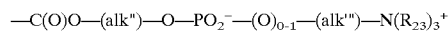

wherein $R_{23}$ is hydrogen or $C_1$–$C_6$-alkyl; $An^-$ is an anionic group —$COO^-$, —$SO_3^-$, —$OSO_3^-$ or —$OPO_3H^-$, preferably —$COO^-$ or —$SO_3^-$ and most preferably —$SO_3^-$, alk' is $C_1$–$C_{12}$-alkylene, (alk'') is $C_2$–$C_{24}$-alkylene which is unsubstituted or substituted by a radical —$OY_8$, $Y_8$ is hydrogen or the acyl radical of a carboxylic acid, and (alk''') is $C_2$–$C_8$-alkylene.

(alk') is preferably $C_2$–$C_8$-alkylene, more preferably $C_2$–$C_6$-alkylene and most preferably $C_2$–$C_4$-alkylene. (alk'') is preferably $C_2$–$C_{12}$-alkylene, more preferably $C_2$–$C_6$-alkylene and particularly preferably $C_2$–$C_3$-alkylene which is in each case unsubstituted or substituted by hydroxy or by a radical —$OY_8$. (alk''') is preferably $C_2$–$C_4$-alkylene and more preferably $C_2$–$C_3$-alkylene. $R_9$ is hydrogen or $C_1$–$C_4$-alkyl, more preferably methyl or ethyl and particularly preferably methyl. A preferred zwitterionic substituent of B or B' is of formula

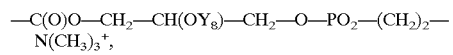

wherein $Y_8$ is hydrogen or the acyl radical of a higher fatty acid.

B denotes for example a radical of formula

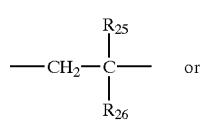

(7a)

or

-continued

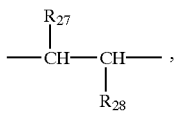
(7b)

wherein $R_{25}$ is hydrogen or $C_1$–$C_4$-alkyl, preferably hydrogen or methyl; $R_{26}$ is a hydrophilic substituent, wherein the above given meanings and preferences apply; $R_{27}$ is $C_1$–$C_4$-alkyl, phenyl or a radical —C(O)O$Y_9$, wherein $Y_9$ is hydrogen or unsubstituted or hydroxy-substituted $C_1$–$C_4$-alkyl; and $R_{28}$ is a radical —C(O)$Y_9'$ or —CH$_2$—C(O)O$Y_9'$ wherein $Y_9'$ independently has the meaning of $Y_9$.

$R_{27}$ is preferably $C_1$–$C_2$-alkyl, phenyl or a group —C(O)O$Y_9$. $R_{28}$ is preferably a group —C(O)O$Y_9'$ or —CH$_2$—C(O)O$Y_9'$ wherein $Y_9$ and $Y_9'$ are each independently of the other hydrogen, $C_1$–$C_2$-alkyl or hydroxy-$C_1$–$C_2$-alkyl. Particularly preferred —CHR$_{27}$—CHR$_{28}$— units according to the invention are those wherein $R_{27}$ is methyl or a group —C(O)O$Y_9$ and $R_{28}$ is a group —C(O)O$Y_9'$ or —CH$_2$—C(O)O$Y_9'$ wherein $Y_9$ and $Y_9'$ are each hydrogen, $C_1$–$C_2$-alkyl or hydroxy-$C_1$–$C_2$-alkyl.

B' independently may have one of the meanings given above for B.

If (oligomer$^1$) is a radical of formula (6a), the radical -(alk)-S-[B]$_p$-[B']$_q$-Q preferably denotes a radical of formula

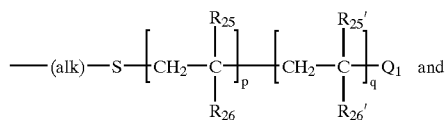
(6a')

and even more preferably of the formula

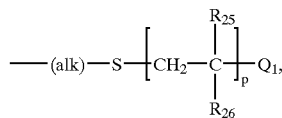
(6a'')

wherein for (alk) $R_{25}$, $R_{26}$, $Q_1$, p and q the above-given meanings and preferences apply, for $R_{25}'$ independently the meanings and preferences given before for $R_{25}$ apply, and for $R_{26}'$ independently the meanings and preferences given before for $R_{26}$ apply.

A preferred radical Z or Z' is, for example a radical of formula

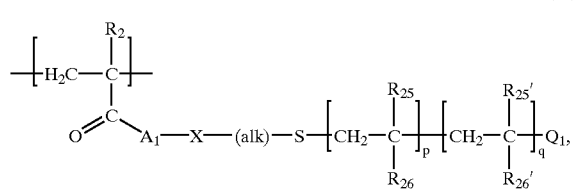
(3a)

wherein $R_2$ is hydrogen or methyl, $A_1$ is —O—(CH$_2$)$_{2-4}$—, —O—CH$_2$—CH(OH)—CH$_2$— or a radical —O—(CH$_2$)$_{2-4}$—NH—C(O)—, X is —O— or —NH—, (alk) is $C_2$–$C_4$-alkylene, $Q_1$ is a monovalent group that is suitable to act as a polymerization chain-reaction terminator, p is an integer from 5 to 50, $R_{25}$ and $R_{25}'$ are each independently of the other hydrogen or methyl, and for $R_{26}$ and $R_{26}'$ each independently the above given meanings and preferences apply.

A particularly preferred radical Z or Z' is, for example, of the formula

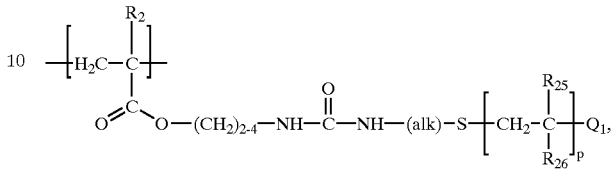
(3b)

wherein for $R_2$, $R_{25}$, $R_{26}$, $Q_1$, (alk) and p the above-given meanings and preferences apply. A particularly preferred group of radicals of the above formula (3b) are those wherein $R_2$ is hydrogen or methyl, (alk) is $C_2$–$C_4$-alkylene, $R_{25}$ is hydrogen or methyl, p is an integer of 5 to 50, Q is as defined before, and for $R_{26}$ the above given meanings and preferences apply; in particular $R_{26}$ of this embodiment is a radical —CONH$_2$, —CON(CH$_3$)$_2$ or

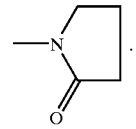

If (oligomer$^1$) is a radical (ii) of formula (6b), Q' in formula (6b) is for example $C_1$–$C_{12}$-alkyl, phenyl or benzyl, preferably $C_1$–$C_2$-alkyl or benzyl and in particular methyl. $R_{19}$ is preferably unsubstituted or hydroxy-substituted $C_1$–$C_4$-alkyl and in particular methyl, u is preferably an integer from 2 to 150, more preferably from 5 to 100, even more preferably from 5 to 75 and particularly preferably from 5 to 50.

If (oligomer$^1$) is a radical of formula (6b'), the above given meanings and preferences apply for the variables $R_{19}$ and u contained therein. $X_2$ in formula (6b') is preferably hydroxy or amino.

If (oligomer$^1$) denotes a radical (iv) of formula (6c), $R_{20}$ and $R_{20}'$ are each preferably ethyl or in particular methyl; v is preferably an integer from 2 to 150, more preferably from 5 to 100, even more preferably from 5 to 75 and particularly preferably from 5 to 50; Q'' is for example hydrogen; and An$^-$ is as defined before.

If (oligomer$^1$) denotes an oligopeptide radical (v) of formula (6d) or 6d'), $R_{21}$ is for example hydrogen, methyl, hydroxymethyl, carboxymethyl, 1-hydroxyethyl, 2-carboxyethyl, isopropyl, n-, sec. or iso-butyl, 4-amino-n-butyl, benzyl, p-hydroxybenzyl, imidazolylmethyl, indolylmethyl or a radical —(CH$_2$)$_3$—NH—C(=NH)—NH$_2$. t is preferably an integer from 2 to 150, more preferably from 5 to 100, even more preferably from 5 to 75 and particularly preferably from 5 to 50.

If (oligomer$^1$) denotes a polyoxyalkylene radical (vi) of formula (6e), $R_{34}$ is preferably hydrogen or $C_1$–$C_{18}$-alkyl, more preferably hydrogen or $C_1$–$C_{12}$-alkyl, even more preferably hydrogen, methyl or ethyl, and particularly preferably hydrogen or methyl. (alk**) is preferably a $C_2$–$C_3$-alkylene radical. z is preferably 0. r and s are each independently preferably an integer from 0 to 100 wherein the total of (r+s) is 5 to 100. r and s are each independently more preferably an integer from 0 to 50 wherein the total of (r+s) is 8 to 50. In a particularly preferred embodiment of the polyoxyalkylene radicals (oligomer), r is an integer from 8 to 50 and particularly 9 to 25, and s is 0.

(oligomer¹) as the radical of an oligosaccharide (vii) may be, for example, a di- or polysaccharide including carbohydrate containing fragments from a biopolymer. Examples are the radical of a cyclodextrin, trehalose, cellobiose, maltotriose, maltohexaose, chitohexaose or a starch, hyaluronic acid, deacetylated hyaluronic acid, chitosan, agarose, chitin 50, amylose, glucan, heparin, xylan, pectin, galactan, glycosaminoglycan, mucin, dextran, aminated dextran, cellulose, hydroxyalkylcellulose or carboxyalkylcellulose oligomer, each of which with a molecular weight average weight of, for example, up to 25000, preferably up to 10000. Preferably the oligosaccharide according to (vii) is the radical of a cyclodextrin with a maximum of 8 sugar units.

Formulae (2), (3a), (6a), or (6e) are to be understood as a statistic description of the respective oligomeric radicals, that is to say, the orientation of the monomers and the sequence of the monomers (in case of copolymers) are not fixed in any way by said formulae. The arrangement of Z and Z' in formula (2), the 1,2 ethylene units in formula (3a), B and B' in formula (6a) or of the ethyleneoxide and propyleneoxide units in formula (6e) thus in each case may be random or blockwise.

The weight average molecular weight of the hydrophilic side chains of the radicals Z or Z' is for example $\geq 200$, preferably from 200 to 25000, more preferably from 300 to 12000, even more preferably from 300 to 8000, most preferably from 300 to 5000 and particularly preferably from 500 to 4000.

The hydrophilic telomers of formula (1) may be prepared, for example, according to PCT application WO 92/09639 by copolymerizing one or more hydrophilic ethylenically unsaturated monomers underlying the radicals Z and optionally Z' in the presence of a functional chain transfer agent such as cysteamine hydrochloride, thioglycolic acid or the like. If desired, the group T then may be further modified in order to introduce an epoxy group or the like.

The ethylenically unsaturated monomers underlying the radicals Z or Z' wherein $R_3$ is a radical —$COOY_{10}$ or —$CONY_{10}Y_{11}$ or the like are known or may be prepared according to methods that are known per se. For example, (meth)acryloylchloride is reacted with a polyethyleneoxide or a Jeffamine, or an isocyanatoalkyl(meth)acrylate is reacted with a polyethyleneoxide or a saccharide.

The ethylenically unsaturated monomers underlying the radicals Z or Z' wherein $R_3$ is a radical of formula (4) may be prepared, for example, by reacting a compound of formula

(8)

wherein R, $R_1$ and $R_2$ each have the above-given meaning and A* is, for example, a group —C(O)—A, wherein A is halogen, particularly chlorine, an ester group an oxyalkylene radical comprising an epoxy group, for example the radical

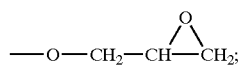

or is a radical —O—$C_2$-$C_{12}$-alkylene-N=C=O; or A* is a radical —$(A_2)_m$—N=C=O, wherein $A_2$ and m have the above-given meaning, with a compound of formula HX-(oligomer¹)  (9), wherein X has the above-given meaning.

The reactions of a compound of formula (8) having a carboxylic acid halide group, an epoxy group or an isocyanato group with an amino or hydroxy compound of formula (9) are well-known in the art and may be carried out as desribed in textbooks of organic chemistry. For example, the reaction of an isocyanato derivative of formula (8) with a compound of formula (9) may be carried out in an inert organic solvent such as an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone or even a lower alcohol, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. In addition, the reaction of an isocyanato derivative of formula (8) with a compound of formula (9) wherein —XH is an amino group also may be carried out in an aqueous solution in the absence of a catalyst. It is advantageous to carry out the above reactions under an inert atmosphere, for example under an nitrogen or argon atmosphere.

Moreover, the ethylenically unsaturated monomers underlying the radicals Z or Z' wherein $R_3$ is a radical of formula (4) and A is a radical of formula (5c) or (5e) may be obtained by reacting a compound of formula

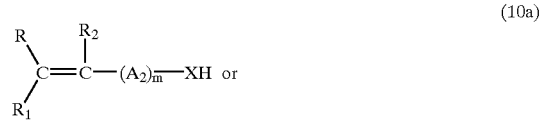

(10a)

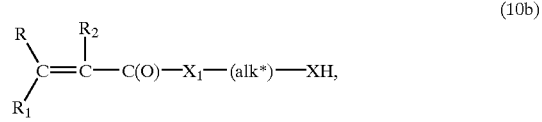

(10b)

wherein R, $R_1$, $R_2$, $A_2$, X, $X_1$, (alk*) and m each have the above-given meaning, with a compound of formula —$X_1'$(O)C— (oligomer¹)  (11), wherein (oligomer¹) has the above-given meaning and $X_1'$ is for example —OH or halogen, in particular chlorine, or together with —(O)C— forms a carboxy anhydride group, in a manner known per se.

The ethylenically unsaturated monomers underlying the radicals Z or Z' wherein $R_3$ is a radical of formula (4), A is a direct bond and (oligomer¹) is a radical of formula (6c') are known or may be prepared according to methods known in the art, for example as described in S. Kobayashi et al., Polymer Bulletin 13, p 447–451 (1985).

Likewise, the ethylenically unsaturated monomers of the formula

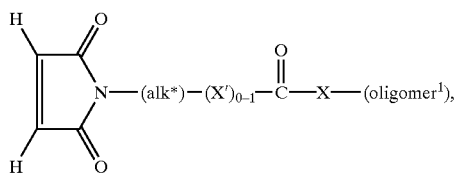
(5f')

wherein (alk*), X', X and (oligomer¹) each have the above-given meaning, may be obtained in a manner known per se, for example, by reacting a compound of formula

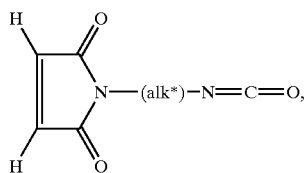
(12)

wherein (alk*) has the above-given meaning, with a compound of the above-given formula (6), or by reacting a compound of formula

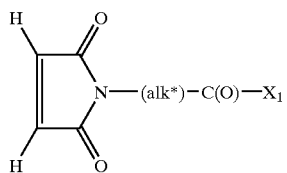
(12a)

with a compound of the above formula (9) wherein (alk*) and $X_1$ each have the above-given meaning.

The compounds of the formula (8), (9), (10a), (10b), (11), (12) and (12a) are known compounds which are commercially available or may be prepared according to known methods. For example, compounds of the formula (9) and (11) wherein (oligomer¹) denotes a radical of formula (6a) may be prepared according to PCT application WO 92/09639 by copolymerizing one or more hydrophilic ethylenically unsaturated monomers in the presence of a functional chain transfer agent such as cysteamine hydrochloride, thioglycolic acid or the like.

Examples of materials that may be coated according to the process of the invention are quartz, ceramics, glasses, silicate minerals, silica gels, metals, metal oxides, carbon materials such as graphite or glassy carbon, natural or synthetic organic polymers, or laminates, composites or blends of said materials, in particular natural or synthetic organic polymers which are known in large number. Some examples of polymers are polyaddition and polycondensation polymers (polyurethanes, epoxy resins, polyethers, polyesters, polyamides and polyimides); vinyl polymers (polyacrylates, polymethacrylates, polystyrene, polyethylene and halogenated derivatives thereof, polyvinyl acetate and polyacrylonitrile); elastomers (silicones, polybutadiene and polyisoprene); or modified or unmodified biopolymers (collagen, cellulose, chitosan and the like).

A preferred group of materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoropolyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene propylene, or tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another preferred group of materials to be coated are those being conventionally used for the manufacture of biomedical devices, e.g. contact lenses, which are hydrophilic per se, since reactive groups, e.g. carboxy, carbamoyl, sulfate, sulfonate, phosphate, amine, ammonium or hydroxy groups, are inherently present in the material and therefore also at the surface of a biomedical device manufactured therefrom. Such materials are known to the skilled artisan and comprise for example polyhydroxyethyl acrylate, polyhydroxyethyl methacrylate (HEMA), polyvinyl pyrrolidone (PVP), polyacrylic acid, polymethacrylic acid, polyacrylamide, polydimethylacrylamide (DMA), polyvinyl alcohol or copolymers for example from two or more monomers from the group hydroxyethyl acrylate, hydroxyethyl methacrylate, N-vinyl pyrrolidone, acrylic acid, methacrylic acid, acrylamide, dimethyl acrylamide, vinyl alcohol and the like. Typical examples are e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon or Atlafilcon.

Still another group of preferred materials to be coated are amphiphilic segmented copolymers comprising at least one hydrophobic segment and at least one hydrophilic segment which are linked through a bond or a bridge member. Examples are silicone hydrogels, for example those disclosed in PCT applications WO 96/31792 and WO 97/49740 which are herewith incorporated by reference.

The material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or a composite made therefrom.

Moreover, the material to be coated may also be an inorganic or metallic base material with or without suitable reactive groups, e.g. ceramic, quartz, or metals, such as silicon or gold, or other polymeric or non-polymeric substrates. E.g. for implantable biomedical applications, ceramics or carbohydrate containing materials such as polysaccharides are very useful. In addition, e.g. for biosensor purposes, dextran coated base materials are expected to reduce nonspecific binding effects if the structure of the coating is well controlled. Biosensors may require polysaccharides on gold, quartz, or other non-polymeric substrates.

The form of the material to be coated may vary within wide limits. Examples are particles, granules, capsules, fibres, tubes, films or membranes, preferably moldings of all kinds such as ophthalmic moldings, in particular contact lenses.

According to step (b) of the invention, one or more different hydrophilic telomers of formula (1) are covalently bound to the surface of the material to be modified on its surface, for example, via reaction of a functional group of the material surface with the group T of the telomer of formula (1).

Suitable functional groups may be inherently (a priori) present at the surface of the material to be modified on its surface. If substrates contain too few or no reactive groups, the material surface can be modified by methods known per se, for example plasma chemical methods (see, for example, WO 94/06485 or WO 98/28026), or conventional functionalization with groups such as —OH, —NH$_2$ or —CO$_2$H produced. Suitable functional groups may be selected from a wide variety of groups well known to the skilled artisan. Typical examples are e.g. hydroxy groups, amino groups, carboxy groups, carbonyl groups, aldehyde groups, sulfonic acid groups, sulfonyl chloride groups, isocyanato groups, carboxy anhydride groups, lactone groups, azlactone groups, epoxy groups and groups being replaceable by amino or hydroxy groups, such as halo groups, or mixtures thereof. Preferred functional groups on the material surface are amino, carboxy, carboxy anhydride, lactone, azlactone or isocyanato groups, in particular amino, carboxy anhydride, epoxy, azlactone or isocyanato groups.

A preferred method for attaching reactive groups to the material surface comprises the plasma induced polymerization of an ethylenically unsaturated compound carrying a reactive group on the material surface according to the method as described in WO 98/28026. Suitable ethylenically unsaturated monomers which may be used in this process are any polymerizable unsaturated compound which carries reactive groups and can be evaporated and introduced into a plasma generating apparatus to contact the material to be coated provided therein. Examples of reactive groups to be contemplated herein include isocyanate (—NCO), isothiocyanate (—NCS), epoxy, anhydride, azlactone and lactone (e.g. β-, γ-, δ-lactone) groups. Specific examples of preferred ethylenically unsaturated compounds carrying reactive groups are 2-isocyanatoethyl-methacrylate (IEM), glycidyl methacrylate, (meth)acrylic acid anhydride and 4-vinyl-2,2-dimethylazlactone.

One preferred embodiment of step (b) of the process of the invention comprises providing an amino or hydroxy group modified material surface and reacting said amino or hydroxy groups with a hydrophilic telomer of formula (1), wherein T is carboxy or a carboxy derivative. Another preferred embodiment of step (b) of the process of the invention comprises providing a material surface comprising carboxy, carboxy anhydride, lactone, azlactone or isocyanato groups and reacting said reactive groups with a hydrophilic telomer of formula (1), wherein T is amino.

The reactions of the reactive groups on the material surface to be coated with the hydrophilic telomer of formula (1) are well-known in the art and may be carried out as desribed in textbooks of organic chemistry. For example, in case that the material surface to be coated has been previously modified to carry isocyanato groups, the reaction of the isocyanato groups with a compound of formula (1) wherein T is an hydroxy or amino group may be carried out in an inert organic solvent such as acetonitrile, an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. In addition, the reaction of the isocyanato groups of the primary coating with a compound of formula (3) wherein X is an amino group also may be carried out in an aqueous solution in the absence of a catalyst. It can be advantageous to carry out the above reactions under an inert atmosphere, for example under an nitrogen or argon atmosphere.

In case that the material surface to be coated has been previously modified to carry azlactone groups, the reaction of the azlactone groups with a compound of formula (1) wherein T is an amino or hydroxy group, may be carried out at room temperature or at elevated temperature, for example at about 20 to 75° C., in water, in a suitable organic solvent or mixtures thereof, for example in an aqueous medium or in an aprotic polar solvent such as DMF, DMSO, dioxane, acetonitrile and the like.

In case that the material surface to be coated has been previously modified to carry epoxy groups, the reaction of the epoxy groups with a compound of formula (1) wherein T is an amino group may be carried out, for example, at room temperature or at elevated temperature, for example at about 20 to 100° C., in water, in a suitable organic solvent or in mixtures thereof.

In case that the material surface to be coated has been previously modified to carry epoxy groups, the reaction of the epoxy groups with a compound of formula (1) wherein T is a hydroxy group may be carried out, for example, at room temperature or at elevated temperature, for example at about 20 to 100° C., in an aprotic medium using a base catalyst, for example Al(O—C$_1$–C$_6$-alkyl)$_3$ or Ti(O—C$_1$–C$_6$-alkyl)$_3$. The same applies to the reaction of a hydroxy group modified surface with a compound of formula (1) wherein T is an epoxy group.

In case that the material surface to be coated has been previously modified to carry carboxy anhydride groups, the reaction of the carboxy anhydride with a compound of formula (1) wherein T is an amino or hydroxy group may be carried out as described in organic textbooks, for example in an aprotic solvent, for example one of the above-mentioned aprotic solvents, at a temperature from room temperature to about 100° C.

In case that the material surface to be coated has been previously modified to carry carboxy groups, the reaction of the carboxy groups with the hydroxy, amino or epoxy groups T of a compound of formula (1), or the reaction of an amino or hydroxy group modified surface with a compound of formula (1), wherein T is carboxy, may be carried out under the conditions that are customary for ester or amide formation, for example in an aprotic medium at a temperature from about room temperature to about 100° C. It is further preferred to carry out the esterification or amidation reaction in the presence of an activating agent, for example N-ethyl-N'-(3-dimethyl aminopropyl)carbodiimide (EDC), N-hydroxy succinimide (NHS) or N,N'-dicyclohexyl carbodiimide (DCC).

The coated material obtained according to the invention may be purified afterwards in a manner known per se, for example by washing or extraction with a suitable solvent such as water.

According to the process of the invention, the material surface to be modified is provided with a coating having a so-called bottle brush-type structure (BBT) composed of tethered "hairy" chains. The BBT structure of the coatings of the invention may be varied within wide limits, for example, by a suitable choice of the hydrophilic telomer of formula (1). Such BBT structures in one embodiment comprise a long hydrophilic or hydrophobic backbone which carries relatively densely packed comparatively short hydrophilic side chains (called primary bottle brushes). Another embodiment relates to secondary bottle brushes which are characterized in that the hydrophilic side chains themselves carry densely packed hydrophilic "secondary" side chains. Polymeric coatings of said primary and secondary BBT structures to a certain extent mimic highly water-retaining structures occurring in the human body, for example in cartilage or mucosal tissue.

The coating thickness of the coated material surfaces obtained according to the process of the invention depends principally on the desired properties. It can be, for example, from 0.001 to 1000 μm, preferably from 0.005 to 100 μm, more preferably from 0.01 to 50 μm, even more preferably from 0.01 to 5 μm, especially preferably from 0.01 to 1 μm and particularly preferably from 0.01 to 0.5 μm.

A further embodiment of the invention relates to a material that is coated by the process of the invention.

The material that is coated by the process of the invention is, for example, an organic bulk material, preferably a biomedical device, e.g. an ophthalmic device, preferably a contact lens including both hard and particularly soft contact lenses, an intraocular lens or artificial cornea. Further examples are materials useful for example as wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

The biomedical devices, e.g. ophthalmic devices obtained according to the invention have a variety of unexpected advantages over those of the prior art which make those devices very suitable for practical purposes,e.g. as contact lens for extended wear or intraocular lens. For example, they do have a high surface wettability which can be demonstrated by their contact angles, their water retention and their water-film break up time or pre-lens or on-eye tear film break up time (TBUT).

The TBUT plays an particularly important role in the field of ophthalmic devices such as contact lenses. Thus the facile movement of an eyelid over a contact lens has proven important for the comfort of the wearer; this sliding motion is facilitated by the presence of a continuous layer of tear fluid on the contact lens, a layer which lubricates the tissue/lens interface. However, clinical tests have shown that currently available contact lenses partially dry out between blinks, thus increasing friction between eyelid and the lens. The increased friction results in soreness of the eyes and reduced movement of the contact lenses. Now it has become feasible to considerably increase the TBUT of commercial contact lenses such as, for example, Focus Dailies™, Focus New Vues® or Lotrafilcon A lenses, by applying a surface coating according to the invention. On the base curve of a contact lens, the pronounced lubricity of the coating facilitates the on-eye lens movement which is essential for extended wear of contact lenses. Moreover, the materials obtained by the process of the invention provide additional effects being essential for lenses for extended wear, such as an increased thickness of the pre-lens tear film which contributes substantially to low microbial adhesion and resistance to deposit formation. Due to the extremely soft and lubricious character of the novel surface coatings, biomedical articles such as in particular contact lenses coated by the process of the invention show a superior wearing comfort including improvements with respect to late day dryness and long term (overnight) wear. The novel surface coatings moreover interact in a reversible manner with occular mucus which contributes to the improved wearing comfort.

In addition, biomedical devices, e.g. ophthalmic devices such as contact lenses, coated by the process of the invention, have a very pronounced biocompatibility combined with good mechanical properties. For example, the devices are blood compatible and have a good tissue integration. In addition, there are generally no adverse eye effects observed, while the adsorption of proteins or lipids is low, also the salt deposit formation is lower than with conventional contact lenses. Generally, there is low fouling, low microbial adhesion and low bioerosion while good mechanical properties can be for example found in a low friction coefficient and low abrasion properties. Moreover, the dimensional stability of the materials obtained according to the invention is excellent. In addition, the attachment of a hydrophilic surface coating at a given bulk material according to the invention does not affect its visual transparency.

In summary, the ophthalmic devices obtained by the process of the invention, such as contact lenses and artificial cornea, provide a combination of low spoilation with respect to cell debris, cosmetics, dust or dirt, solvent vapors or chemicals, with a high comfort for the patient wearing such opthalmic devices in view of the soft hydrogel surface which for example provides a very good on-eye movement of the ohthalmic device.

Biomedical devices such as renal dialysis membranes, blood storage bags, pacemaker leads or vascular grafts coated by the process of the invention resist fouling by proteins by virtue of the continuous layer of bound water, thus reducing the rate and extent of thrombosis. Blood-contacting devices fabricated according to the present invention are therefore haemocompatible and biocompatible.

In the examples, if not indicated otherwise, amounts are amounts by weight, temperatures are given in degrees Celsius. Tear break-up time values in general relate to the pre-lens tear film non-invasive break-up time (PLTF-NIBUT) that is determined following the procedure published by M. Guillon et al., Ophthal. Physiol. Opt. 9, 355–359 (1989) or M. Guillon et al., Optometry and Vision Science 74, 273–279 (1997). Average advancing and receding water contact angles of coated and non-coated lenses are determined with the dynamic Wilhelmy method using a Krüss K-12 instrument (Kruss GmbH, Hamburg, Germany). Wetting force on the solid is measured as the solid is immersed in or withdrawn from a liquid of known surface tension.

Preparation of Functionalized Contact Lens Surfaces

EXAMPLE A-1

1,2-Diaminocyclohexane Plasma Coating (DACH)

Two dried Lotrafilcon A lenses (polysiloxane/ perfluoroalkyl polyether copolymer) are, after extraction in isopropanol, toluene and again in isopropanol, placed on the glass holder within the plasma reactor equipped with an external ring electrode and a 27.13 MHz radiofrequency (RF) generator for the generation of an inductively-coupled, cold glow discharge plasma. The distance between the substrates and the lower edge of the plasma zone is 12 cm. The reactor is evacuated to a pressure of 0.008 mbar, and held at these conditions for one hour. Then, the argon plasma gas flow rate into the plasma zone of the reactor is set to 20 sccm (standard cubic centimeter), the pressure in the reactor is adjusted to 0.12 mbar and the RF generator is switched on. The plasma discharge of a power 250 Watts is maintained for a total period of 1 min (in order to clean and activate the lenses surfaces). Afterward the 1,2-DACH vapor is introduced into the reactor chamber from DACH reservoir (maintained at 24° C.) at 0.15 mbar for 1 min. After this, the following parameters for the plasma polymerization of DACH are chosen: Argon flow rate for plasma excitation=5 sccm, Argon carrier gas flow rate for DACH transport=5 sccm, temperature of the DACH evaporation unit=24° C., the distance between the lower edge of the plasma zone and the substrates=5 cm, pressure=0.2 mbar, and plasma power= 100 W. The lenses are treated for about 5 minutes with a pulsing glow discharge plasma (1 μsec. on, 3 μsec. off). After 5 minutes of deposition the plasma discharge is interrupted and DACH vapor is let to flow into reactor for other 5 min. The reactor is then evacuated and maintained for 30 minutes at a pressure 0.008 mbar in order to remove residual monomer and activated spices. The internal pressure is brought to atmospheric by using dry nitrogen. The substrates are then turned over and the whole procedure is repeated to coat the other side of the substrates. The samples are then unloaded from the reactor and used for the subsequent photoinitiator linkage.

EXAMPLE A-2

Plasma-induced Polymerization of 2-isocyanatoethyl Methacrylate (IEM)

IEM is plasma induced polymerized on Lotrafilcon A lenses (polysiloxane/perfluoroalkyl polyether copolymer) according to the method as described in WO 98/28026, Example B-1, B-2, B-3 or B-4 on pages 31–33.

EXAMPLE A-3

Plasma-induced Polymerization of Glycidylmethacrylate (GMA)

GMA is plasma induced polymerized on Lotrafilcon A lenses (polysiloxane/perfluoroalkyl polyether copolymer) according to the method as described in WO 98/28026, Example B-5, on page 33.

EXAMPLE A-4

Plasma-induced Polymerization of 4-vinyl-2,2-dimethyl Azlactone (VAL)

VAL is plasma induced polymerized on Lotrafilcon A lenses (polysiloxane/perfluoroalkyl polyether copolymer) according to the method as described in WO 98/28026, Example B-7, on page 34.

EXAMPLE A-5

Plasma-induced Polymerization of Acrylic Acid Anhydride (AAnh)

AAnh is plasma induced polymerized on Lotrafilcon A lenses (polysiloxane/perfluoroalkyl polyether copolymer) according to the method as described in WO 98/28026, Example B-6, on page 34.

Preparation of Monofunctional Bottle-brush (BB) Type Telomers

EXAMPLE B-1

Telomer from α,α'-mono-isocyanatoethyl Methacrylato Trehalose

A 100 mL three-necked round bottom flask is charged with a solution of 3.8 g (33.4 mmol) cysteamine hydrochloride in 45 mL of 0.1 molar aqueous acetic acid. 55 mg (0.2 mmol) α,α'-azodiisobutyramidine dihydrochloride and 53 g (106 mmol) mono-isocyanatoethyl methacrylato trehalose are added. An intensive cooler and an internal thermometer are connected to the flask. The apparatus is evacuated to 100 mbar and filled with argon. This is repeated five times. The mixture is heated overnight to 60° C. and then cooled to room temperature. The product precipitates in 2 liters of acetone and is isolated by filtration, yielding a slightly yellow colored powder. No resonances corresponding to C=C double bonds can be detected by $^1$H-NMR spectroscopy, indicating >98% conversion of the monomer.

The product is dissolved in 200 mL water and the pH is adjusted to 10.5 by addition of 107 mL 0.1 molar sodium hydroxide solution and then diluted with water to a total volume of 500 mL. Salts and residual low molecular weight components are removed by ultrafiltration using a UFP-1-E-4A cartridge from A/G Technology Corporation, Needham, Mass. The concentration of amino-groups is determined by functional group titration, result 0.12 mmol/g $NH_2$ corresponding to an average molecular weight of the telomer of 8300 g/mol and a degree of polymerization of 16.

EXAMPLE B-2

Monocarboxy-terminated Telomer from Methacryloyloxy-poly-ethyleneglycol-methylether A 100 ml three-necked round bottom flask is charged with a solution of 50.0 g (100 mmoles) of methacryloyloxy-polyethyleneglycol-methylether (Blemer PME 400, n~9), 400.5 mg (4.35 mmoles) of thioglycolic acid, 64.7 mg (0.2 mmoles) of initiator 2,2 Azo-bis-(N,N-dimethyleneisobutyro-amidine)-dihydro-chloride and 200 ml of water (HPLC quality). To the clear solution formed 2 drops of 0,2 N aqueous HCl solution are added. Dissolved oxygen is removed from the solution by 3 repeat cycles of evacuation at 10 Torr and 5 minutes of nitrogen bubbling through the solution. The mixture is then kept under a nitrogen blanket and heated under stirring to 45° C. for two hrs., followed by 4 hrs. at 40° C. The clear solution is then purified from low molecular weight components by 24 hrs of dialysis against distilled water using a dialysis tube with a cut-off limit of 1000 Da. The distilled water is renewed 3-times during the 24 hrs period. The clear viscous solution is then lyophilized to obtain a slightly yellowish powder. Titration of carboxy end groups gives 0.07 mVal COOH/g which corresponds to an average molecular weight of 1400 Da.

EXAMPLE B-3

Preparation of the N-hydroxy-succinimide (NHS) Ester Derivative of a Monocarboxy-terminated PEG-methacrylate Derived BB-telomer 2 g of the monocarboxy-terminated PEG-methacrylate derived BB-telomer from Example B-2 are dissolved in 20 ml of water (HPLC quality). 87 mg N-(3- dimethylaminopropyl)-N'-ethylcarbodiimide (EDC), dissolved in 1 ml HPLC water, and 60 mg N-hydroxysuccinimide (NHS), dissolved in 1 ml HPLC water, are added to the solution and pH of the mixture is adjusted to 4.5 with 0.1M HCl. The mixture is then stirred at RT for 15 minutes and filtered through 0.22 μm filter. The solution obtained after filtration is directly used for the surface modification process.

Binding of Monofunctional Bottle-brush-type Telomers to Functionalized Contact Lens Surfaces

EXAMPLE C-1

Surface Binding of Monoamino-terminated IEM-trehalose Derived BB-telomer to Isocyanato-functional Contact Lens Surface In a 10 ml Erlenmeier flask with glas stopper 500 mg of the trehalose containing BB-telomer prepared according to Example B-1 are dissolved in 5 ml of water (HPLC quality). Three contact lenses as prepared according to Example A-2 are added. The lenses are treated under gentle shaking at room temperature for 10 hrs. The lenses are then rinsed with water and extracted with water using a small Soxhlet apparatus for 4 hrs. In order to prove the firm covalent surface binding of the BB-telomer the lenses are then autoclaved in water at 121° C. for 20 minutes. Wettability tests are accomplished on the lenses by determination of dynamic contact angles.

| Contact angles: | Advancing | Receding | Hysteresis |
|---|---|---|---|
| Treated lenses | 27° | 13° | 14° |
| Untreated lenses | 104° | 96° | 8° |

EXAMPLES C-2 TO C-5

According to the procedure described in Example C-1 the IEM-trehalose derived monoamino-terminated BB-telomer from Example B-1 is applied to treat surface-functionalized contact lenses prepared according to Examples A-3, A-4 and A-5.

| Contact lenses from example | Solvent/Temperature used | Contact Angles | |
|---|---|---|---|
| | | advancing | receding |
| A-3 | water/50° C. | 43° | 26° |
| A-4 | water/25° C. | 18° | 11° |
| A-5 | DMSO/25° C. | 29° | 17° |

EXAMPLE C-6

Binding of Monocarboxy-terminated PEG-methacrylate Derived BB-telomer to Amino-functional Contact Lens Surfaces Following the procedure as outlined under Example C-1 contact lenses which have been amino-functionalized by a DACH plasma tretament according to example A-1 are grafted with the monocarboxy-terminated PEG BB-telomer prepared according to Example B-2. In order to facilitate the condensation reaction 100 mg of the water soluble carbodiimide derivative EDC are added to the aqueous solution of the telomer. Autoclaving and contact angle measurements confirm the successful surface modification of the contact lenses.

| Contact angles | Advancing | Receding | Hysteresis |
|---|---|---|---|
| Treated lenses | 57° | 43° | 14° |
| Untreated lenses | 109° | 93° | 16° |

EXAMPLE C-7

Binding of the N-hydroxy-succinimide Ester Derivative of PEG-methacrylate Derived Monocarboxy-terminated BB-telomer to an Aminated Contact Lens Surface Following the procedure as described in Example C-1, 5 ml of an aqueous solution of the activated NHS-ester of the monocarboxy-teminated PEG-methacrylate BB-telomer, prepared according to Example B-3, are used instead of the aqueous solution of the telomer according to Example B-1. The grafting process onto the aminated contact lens surface prepared according to Example A-1 is accomplished at pH 9.0 by stirring at room temperature for 12 hrs. Highly wettable lens surfaces are obtained after extraction with water and autoclaving.

| Contact angles: | Advancing | Receding | Hysteresis |
|---|---|---|---|
| Treated lenses | 48° | 34° | 14° |
| Untreated lenses | 104° | 96° | 8° |

What is claimed is:

1. A process for coating a material surface, comprising the steps of:

(a) providing a hydrophilic telomer of formula $$\text{(oligomer)-T} \quad (1),$$

wherein

T is hydroxy, epoxy, amino, $C_1$–$C_6$-alkylamino, carboxy or a carboxy derivative, and (oligomer) is the radical of a telomer of formula

$$-(\text{Alk})-S-[Z]_a-[Z']_b-Q \quad (2),$$

wherein (Alk) is $C_2$–$C_{12}$-alkylene which may be interrupted by —O— or —NH—, Q is a monovalent group that is suitable to act as a polymerization chain-reaction terminator, a and b are each independently of another an integer from 0 to 350, wherein the total of (a+b) is an integer from 2 to 350, wherein Z and Z' are each independently of the other a radical of the formula

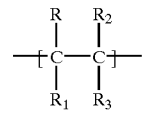

(3)

wherein $R_1$ is hydrogen or $C_1$–$C_6$-alkyl or a radical —COOR';

R, R' and $R_2$ are each independently of the other hydrogen or $C_1$–$C_6$-alkyl; and $R_3$ is a non-ionic substituent selected from the group consisting of a radical —COOY$_{10}$, wherein
Y$_{10}$ is a radical —CH$_2$CH$_2$—O—(CH$_2$CH$_2$O)$_y$—E, E is hydrogen or C$_1$–C$_6$-alkyl and y is an integer from 3 to 24, or Y$_{10}$ is a radical —C$_2$–C$_6$-alkyl-NH—C(O)—O—G wherein —O—G is the radical of a saccharide or is a radical —O—(CH$_2$CH$_2$O)$_y$—E wherein E and y are each as defined above; and a
radical —CONY$_{11}$Y$_{12}$, wherein Y$_{11}$ is hydrogen or unsubstituted or hydroxy-substituted C$_1$–C$_{24}$alkyl, and Y$_{12}$ is C$_1$–C$_{12}$-alkyl which is substituted by a radical —O—(CH$_2$CH$_2$O)$_y$—E and wherein E and y are as defined above; and a zwitter-ionic substituent of formula

—C(O)O—CH$_2$—CH(OY$_{13}$)—CH$_2$—O—PO$_2^-$—(CH$_2$)$_2$—N(CH$_3$)$_3^+$, wherein Y$_{13}$ is the acyl radical of a higher fatty acid, and (b) covalently binding the hydrophilic telomer to the material surface.

2. A process according to claim 1, wherein Z and Z' are each independently of the other a radical of the formula

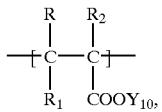 (3')

wherein R and R$_1$ are each hydrogen, R$_2$ is hydrogen or methyl, and Y$_{10}$ is a radical —CH$_2$CH$_2$—O—(CH$_2$CH$_2$O)$_{4-12}$—E or —CH$_2$CH$_2$—NH—C(O)—O—G, wherein —O—G is the radical of a mono- or disaccharide or the radical of an oligosaccharide and E is hydrogen or C$_1$–C$_2$-alkyl.

3. A process according to claim 1, wherein in step (b) the material surface comprises amino or hydroxy groups, and said amino or hydroxy groups are reacted with a hydrophilic telomer of formula (1), wherein T is carboxy or a carboxy derivative.

4. A process according to claim 1, wherein in step (b) the material surface comprises carboxy, carboxy anhydride, lactone, azlactone or isocyanato groups, which are reacted with a hydrophilic telomer of formula (1), wherein T is amino.

5. A coated material that is obtained by the process of claim 1.

6. A coated material according to claim 5, which is a biomedical device.

7. A coated material according to claim 5, which is a contact lens, intraocular lens or artificial cornea.

8. A process for coating a material surface, comprising the steps of:

(a) providing a hydrophilic telomer of formula (oligomer)-T (1), wherein
T is hydroxy, epoxy, amino, C$_1$–C$_6$-alkylamino, carboxy or a carboxy derivative, and
(oligomer) is the radical of a telomer of formula

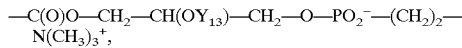 (2), wherein
(Alk) is C$_2$–C$_{12}$-alkylene which may be interrupted by —O— or —NH—, Q is a monovalent group that is suitable to act as a polymerization chain-reaction terminator, a and b are each independently of another an integer from 0 to 350, wherein the total of (a+b) is an integer from 2 to 350, wherein
Z and Z' are each independently of the other a radical of the formula

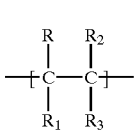 (3)

wherein
R$_1$ is hydrogen or C$_1$–C$_6$-alkyl or a radical —COOR';
R, R' and R$_2$ are each independently of the other hydrogen or C$_1$–C$_6$-alkyl; and R$_3$ is a radical of formula -A-(oligomer$^1$) (4), wherein A is a direct bond or is a radical of formula —C(O)—(A$_1$)$_n$—X— (5a)

or

—(A$_2$)$_m$—NH—C(O)—X— (5b);

or

—(A$_2$)$_m$—X—C(O)— (5c);

or

—C(O)—NH—C(O)—X— (5d);

or

—C(O)—X$_1$-(alk*)-X—C(O)— (5e);

A$_1$ is —O—C$_2$–C$_{12}$-alkylene which is unsubstituted or substituted by hydroxy, or is —O—C$_2$–C$_{12}$-alkylene-NH—C(O)— or —O—C$_2$–C$_{12}$-alkylene-O—C(O)—NH—R$_{33}$—NH—C(O)—, wherein
R$_{33}$ is linear or branched C$_1$–C$_{18}$-alkylene or unsubstituted or C$_1$–C$_4$-alkyl- or C$_1$–C$_4$-alkoxy-substituted C$_6$–C$_{10}$-arylene, C$_7$–C$_{18}$-aralkylene, C$_6$–C$_{10}$-arylene-C$_1$–C$_2$-alkylene-C$_6$–C$_{10}$-arylene, C$_3$–C$_8$-cycloalkylene, C$_3$–C$_8$-cycloalkylene-C$_1$–C$_6$-alkylene, C$_3$–C$_8$-cycloalkylene-C$_1$–C$_2$-alkylene-C$_3$–C$_8$-cycloalkylene or C$_1$–C$_6$-alkylene-C$_3$–C$_8$-cycloalkylene-C$_1$–C$_6$-alkylene;

A$_2$ is C$_1$–C$_8$-alkylene; phenylene or benzylene;
m and n are each independently of the other the number 0 or 1;
X and X$_1$ are each independently of the other a bivalent group —O— or —NR", wherein R" is hydrogen or C$_1$–C$_6$-alkyl;
(alk*) is C$_2$–C$_{12}$-alkylene;

and (oligomer¹) is
(i) the radical of a telomer of formula

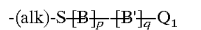 (6a), wherein
(alk) is $C_2$–$C_{12}$-alkylene,
$Q_1$ is a monovalent group that is suitable to act as a polymerization chain-reaction terminator,
p and q are each independently of another an integer from 0 to 350, wherein the total of (p+q) is an integer from 2 to 350,
and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

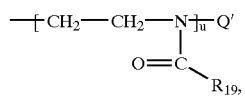 (6b)

wherein $R_{19}$ is hydrogen or unsubstituted or hydroxy-substituted $C_1$–$C_{12}$-alkyl, u is an integer from 2 to 250 and Q' is a radical of a polymerization initiator; or (iii) the radical of formula

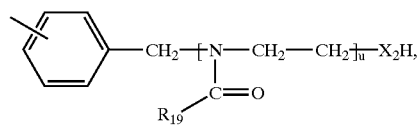 (6b')

wherein $X_2$ is —O—, —NH— or —N$C_1$–$C_6$-alkyl- and $R_{19}$ and u are as defined above, or (iv) the radical of an oligomer of formula

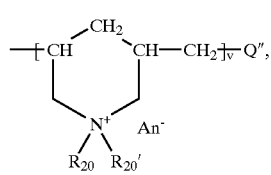 (6c)

wherein $R_{20}$ and $R_{20}'$ are each independently $C_1$–$C_4$-alkyl, An⁻ is an anion, v is an integer from 2 to 250, and Q" is a monovalent group that is suitable to act as a polymerization chain-reaction terminator; or (v) the radical of an oligopeptide of formula

 (6d)

or

 (6d'), wherein $R_{21}$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—NH₂ and t is an integer from 2 to 250, or the radical of an oligopeptide based on proline or hydroxyproline; or (vi) the radical of a polyalkylene oxide of formula

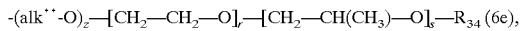

wherein $R_{34}$ is hydrogen or $C_1$–$C_{24}$-alkyl, (alk**) is $C_2$–$C_4$-alkylene, z is 0 or 1, r and s are each independently an integer from 0 to 250 and the total of (r+s) is from 2 to 250; or (vii) the radical of an oligosaccharide; subject to the provisos that
A is not a direct bond if (oligomer) is a radical of formula (6a),
A is a radical of formula (5a), (5b) or (5d) or A and $R_1$, together with the adjacent double bond, are a radical of formula (5f) if (oligomer) is a radical of formula (6b), (6c), (6d) or (6e) or is the radical of an oligosaccharide;
A is a direct bond if (oligomer) is a radical of formula (6b'); and
A is a radical of formula (5c) or (5e) if (oligomer) is a radical of formula (6d'); and (b) covalently binding the hydrophilic telomer to the material surface.

9. A process according to claim 8, wherein (oligomer¹) is a radical of formula

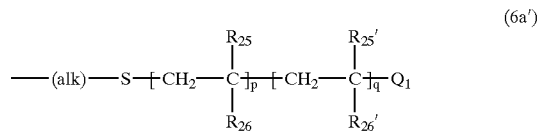 (6a')

wherein (alk) is $C_2$–$C_4$-alkylene, $R_{25}$ and $R_{25}'$ are each independently of the other hydrogen or $C_1$–$C_4$-alkyl, $Q_1$ is a monovalent group that is suitable to act as a polymerization chain-reaction terminator, p and q are each independently of the other an integer of from 0 to 150, wherein the total of (p+q) is from 2 to 150, and $R_{26}$ is a radical —COOY, wherein Y is $C_1$–$C_2$alkyl, $C_2$–$C_3$-alkyl, which is substituted by hydroxy, amino or N,N-di-$C_1$–$C_2$-alkylamino, or is a radical —$C_2$–$C_4$-alkylene-NH—C(O)—O—G wherein —O—G is the radical of trehalose or a cyclodextrin fragment with a maximum of 8 sugar units; a radical —CO—N$Y_1Y_2$, wherein $Y_1$ and $Y_2$ are each independently of the other hydrogen or $C_1$–$C_4$-alkyl which is unsubstituted or substituted by hydroxy, or $Y_1$ and $Y_2$ together with the adjacent N-atom form a N—$C_1$–$C_2$-alkylpiperazino or morpholino ring; or a heterocyclic radical selected from the group consisting of N-pyrrolidonyl, 2- or 4-pyridinyl, 2-methylpyridin-5-yl, 2-, 3-oder 4-hydroxypyridinyl, N-ε-caprolactamyl, N-imidazolyl, 2-methylimidazol-1-yl, N-morpholinyl and 4-N-methylpiperazin-1-yl.

10. A process according to claim 8, wherein T is amino or carboxy, (Alk) is $C_2$–$C_4$-alkylene, Q is a monovalent group that is suitable to act as a polymerization chain-reaction terminator, b is 0, a is an integer from 5 to 100, and Z is a radical of formula

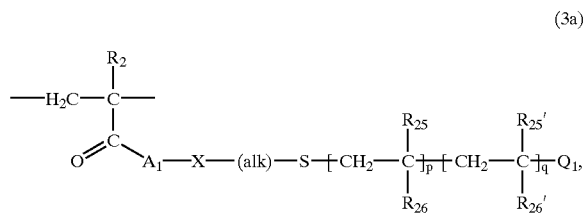 (3a)

wherein
$R_2$ is hydrogen or methyl, $A_1$ is —O—$(CH_2)_{2-4}$—, —O—$CH_2$—CH(OH)—$CH_2$— or a radical —O—

$(CH_2)_{2-4}$—NH—C(O)—, X is —O— or —NH—, (alk) is $C_2$–$C_4$-alkylene, $Q_1$ is a monovalent group that is suitable to act as a polymerization chain-reaction terminator, q is 0, p is an integer from 5 to 50, $R_{25}$ and $R_{25}'$ are each independently of the other hydrogen or methyl, and $R_{26}$ and $R_{26}'$ are each independently of the other a radical —$CONH_2$, —$CON(CH_3)_2$, —CONH—$(CH_2)_2$—OH,

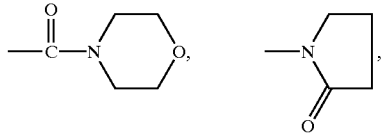

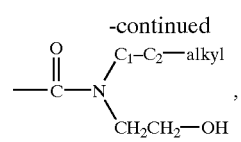

—COO—$(CH_2)_2$—$N(CH_3)_2$, or —COO$(CH_2)_{2-4}$—NHC(O)—O—G wherein —O—G is the radical of trehalose.

11. A coated material that is obtained by the process of claim 8.

12. A coated material according to claim 11, which is a biomedical device.

13. A coated material according to claim 11, which is a contact lens, intraocular lens or artificial cornea.

* * * * *